(12) United States Patent
Schumacher et al.

(10) Patent No.: US 9,861,718 B2
(45) Date of Patent: Jan. 9, 2018

(54) MEASUREMENT OF THE NCG CONCENTRATION IN A STEAM STERILIZER

(71) Applicant: 3M INNOVATIVE PROPERTIES COMPANY, St. Paul, MN (US)

(72) Inventors: Knut Schumacher, Neuss (DE); Robbert-Jan Hermsen, Steijl (NL)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 286 days.

(21) Appl. No.: 14/428,441

(22) PCT Filed: Sep. 16, 2013

(86) PCT No.: PCT/US2013/059909
§ 371 (c)(1),
(2) Date: Mar. 16, 2015

(87) PCT Pub. No.: WO2014/046998
PCT Pub. Date: Mar. 27, 2014

(65) Prior Publication Data
US 2015/0224216 A1    Aug. 13, 2015

(30) Foreign Application Priority Data
Sep. 18, 2012 (GB) .................................. 1216587.4

(51) Int. Cl.
| | | |
|---|---|---|
| *G01N 31/22* | (2006.01) | |
| *A61L 2/28* | (2006.01) | |
| *A61L 2/07* | (2006.01) | |
| *G01N 25/60* | (2006.01) | |
| *G01N 7/14* | (2006.01) | |

(52) U.S. Cl.
CPC ........ *A61L 2/28* (2013.01); *A61L 2/07* (2013.01); *G01N 7/14* (2013.01); *G01N 25/60* (2013.01)

(58) Field of Classification Search
CPC ..................................... A61L 2/00; A61L 2/28
USPC .................................. 436/1, 2; 422/109, 119
See application file for complete search history.

(56) References Cited

U.S. PATENT DOCUMENTS

| | | | |
|---|---|---|---|
| 3,479,131 A | 11/1969 | Scoffield et al. | |
| 4,594,223 A * | 6/1986 | Dyke ........................ | A61L 2/24 422/119 |
| 4,865,814 A | 9/1989 | Childress | |
| 6,323,032 B1 * | 11/2001 | Kuepper ................... | A61L 2/28 422/109 |
| 6,630,352 B1 * | 10/2003 | Reiner ...................... | A61L 2/28 116/216 |
| 2002/0034823 A1 * | 3/2002 | Kuepper ................... | A61L 2/24 436/1 |
| 2003/0087441 A1 | 5/2003 | Lemus et al. | |
| 2005/0260760 A1 | 11/2005 | Hucker | |

(Continued)

FOREIGN PATENT DOCUMENTS

| | | |
|---|---|---|
| DE | 25 58 936 | 7/1977 |
| DE | 36 36 716 | 5/1988 |
| DE | 199 44 847 | 5/2001 |

(Continued)

*Primary Examiner* — Lam Nguyen
(74) *Attorney, Agent, or Firm* — 3M Innovative Properties Company; Carlos M. Téllez (57) ABSTRACT

A method and system for determining steam sterilant quality of a steam sterilizer where the steam sterilant comprises non-condensable gas(es).

15 Claims, 5 Drawing Sheets

(56) References Cited

U.S. PATENT DOCUMENTS

2011/0243181 A1    10/2011    Martel

FOREIGN PATENT DOCUMENTS

| DE | 20 2006 006 926 | 8/2006 |
|---|---|---|
| EP | 0 628 814 | 12/1994 |
| EP | 0 776 669 | 6/1997 |
| EP | 0 841 069 | 5/1998 |
| EP | 0 890 833 | 1/1999 |
| EP | 1 230 936 | 8/2002 |
| JP | H10-501154 | 2/1998 |
| JP | 2013-541369 | 11/2013 |
| JP | 2015-529535 | 10/2015 |
| WO | WO 1993/21964 | 11/1993 |
| WO | WO 1997/12637 | 4/1997 |
| WO | WO 1999/32159 | 7/1999 |
| WO | WO 1999/32160 | 7/1999 |

* cited by examiner

MEASUREMENT OF THE NCG CONCENTRATION IN A STEAM STERILIZER

CROSS REFERENCE TO RELATED APPLICATIONS

This application is a national stage filing under 35 U.S.C. 371 of PCT/US2013/059909, filed Sep. 16, 2013, which claims priority to United Kingdom Application No. 1216587.4, filed Sep. 18, 2012, the disclosure of which is incorporated by reference in their entirety herein.

FIELD

The present disclosure relates to a method for determining steam sterilant quality of a steam sterilizer.

BACKGROUND

A sterilization process carried out in a sterilization chamber of a sterilizer and used to sterilize medical and hospital equipment is only effective if a certain combination of environmental conditions is achieved within the sterilization chamber of the sterilizer. For example, when steam is used as a sterilant, the object of the sterilization process is to bring steam at an appropriate temperature into contact with all surfaces of the articles being sterilized for an appropriate length of time. In some steam sterilizers the process of sterilization is typically conducted in three main phases of a sterilization cycle. In the first phase, air trapped within the article being sterilized, i.e. the load being processed, is removed. The second phase is a sterilizing stage, in which the load is subjected to steam under pressure for a recognized combination of time and temperature, which is known to effect proper sterilization. The third phase is a drying phase in which condensate formed during the first two phases is removed by evacuating the chamber.

Air removal from the sterilization chamber may be achieved in a number of ways. For example, in a gravity steam sterilizer, the principle of gravity displacement is utilized, in which steam entering at the top of the chamber displaces the air which exits through a valve in the base of the chamber. In a prevacuum-type steam sterilizer, on the other hand, air is removed forcibly by deep evacuation of the chamber or by a combination of evacuation and steam injection at either subatmospheric and/or superatmospheric pressures.

Any air which is not removed from the sterilization chamber during the air removal phase of the cycle or which leaks into the chamber during a subatmospheric pressure stage due to, e.g., faulty gaskets, valves or seals, may form air pockets within the load that is being sterilized. Likewise, any non-condensable gases (referred to in the following as NCGs; NCGs are generally understood to be air and other gases which will not condense under the conditions of steam sterilization) that are present in the sterilization chamber or are carried within steam supplied to the chamber may form gas pockets within the load. These air or gas pockets will create a barrier to steam penetration, thereby preventing adequate sterilizing conditions being achieved for all surfaces of the load. This is particularly true when porous materials such as hospital linens or fabrics are being sterilized since the air or gas pockets prohibit the steam from penetrating to the interior layers of such materials.

As a result, proper sterilization may not occur. Therefore, methods and devices had been developed to determine the efficacy or effectiveness of sterilization cycles.

One commonly-used procedure for evaluating the effectiveness of air removal during the air removal phase of a porous load steam sterilization cycle and/or for testing for the presence of non-condensable gases is known as the Bowie-Dick test. The typical Bowie-Dick test pack essentially consists of a stack of freshly laundered towels folded to a specific size, with a chemical indicator sheet placed in the centre of the stack. Chemical indicator test sheets undergo a visible change from one distinct colour to another, for example, from an initial white to a final black colour, upon exposure to the sterilization process. If the air removal within the sterilizer is insufficient, or if non-condensable gases are present during the process in sufficient quantity, an air/gas pocket will form in the centre of the stack thereby preventing steam from contacting the steam sensitive chemical indicator test sheet. The consequence of inadequate steam penetration is a non-uniform colour development across the surface of the chemical indicator test sheet: thus, the presence of the air/gas pocket will be recorded by the failure of the indicator to undergo the complete or uniform colour change indicative of adequate steam penetration.

Biological indicators can also be used to provide information on the effectiveness of a sterilization cycle. Parametric monitoring has also been used to either monitor or control a sterilization cycle to ensure that proper sterilization conditions are attained. For example, in U.S. Pat. No. 4,865,814 an automatic sterilizer is disclosed which includes a microprocessor which monitors both the temperature and pressure levels inside the sterilization chamber and controls a heater to allow both pressure and temperature to reach predetermined levels before starting a timer. Once the timer is started, it is stopped if the pressure or temperature levels drop below a predetermined minimum. Since it is known that the pressure and temperature variables of saturated steam are mutually dependent variables when saturated steam is enclosed in a sealed chamber, monitoring of these two variables can ensure that proper conditions are maintained during the sterilization cycle.

Although it is desirable to monitor environmental conditions within the sterilization chamber itself, it is generally considered more desirable to be able to monitor the environmental conditions within an actual load being sterilized or within a test pack (such as the Bowie-Dick test pack) that represents such a load. However, the typical Bowie-Dick test pack presents many disadvantages. Since the Bowie-Dick test pack is not preassembled, it must be constructed every time the procedure is used to monitor sterilizer performance. The preparation, assembly and use of the Bowie-Dick test pack is time consuming and cumbersome and, moreover, varying factors, such as laundering, pre-humidification, towel thickness and wear, and the number of towels used, alter the test results.

Therefore, alternative sterilizer testing systems have been developed to overcome these limitations. For example, WO 97/12637 describes a sterilant challenge device for use in a sterilizer for determining the efficiency of the air removal stage of a sterilization cycle. The device comprises a tube of thermally-insulating material, the bore of the tube defining a free space which is open at one end for the entry of sterilant and is closed at the other end; a plurality of thermally-conductive masses located around the tube, along the length of the latter, the masses being thermally-separated from one another; and a thermal insulation surrounding the tube and the thermally-conductive masses, whereby the penetration of sterilant along the bore of the tube during a sterilization cycle is inhibited through the accumulation of air and/or non-condensable gas within the free space resulting from the condensation of moisture on the walls of the bore.

Any air pocket formed at the closed end of the tube during an inadequate sterilization cycle will inhibit the entry of sterilant. Detection of sterilant at the closed end by means of a sterilant sensor is then an indication that the sterilization cycle had been effective. In an alternative embodiment of WO 97/12637, a plurality of sterilant sensors are provided along the bore of the tube in order to estimate how far sterilant has penetrated along the bore to more clearly indicate whether or not the sterilization cycle has been effective.

SUMMARY

While aforesaid methods and devices are use in determining the efficacy of a sterilization cycle, such methods and devices do not allow for an effective determination of the quality of steam sterilant (i.e. the amount of NCG in the steam) in the sterilizer. It has been recognized that a method and device to allow such a determination would be advantageous in understanding, e.g. in conjunction with the other data of failures or trends in failures in efficacy of sterilization cycle(s) with a particular sterilizer, besides providing an understanding of the quality of the steam sterilant present in the sterilizer.

The present disclosure is based on the general idea to measure the heat transfer from the inner bore of a tube of a challenge device into a thermal load of said challenge device and to calculate from said heat transfer the amount of non-condensable gas(es) present within said tube as well as the amount of steam sterilant condensed within said tube. From said values one may extract information of the quality of the steam.

The present disclosure provides a method for determining steam sterilant quality of a steam sterilizer. The method comprises the following steps:
a) providing within the sterilizer a challenge device comprising
   a tube having a bore, the bore of the tube defining a free space which is open at one end for the entry of steam sterilant and closed at the other end;
   at least one thermal load having a predetermined heat capacity located around the tube, wherein the at least one thermal load contacts directly or indirectly the tube over a contact surface area and there is a predetermined thermal resistance between the tube and the at least one thermal load;
   a temperature sensor adapted to measure the temperature of the at least one thermal load; as well as
   a pressure sensor adapted to measure pressure in the steam sterilizer and/or a temperature sensor adapted to measure the temperature in the steam sterilizer;
   wherein the challenge device is configured and arranged such that, in use, condensate will flow out of the bore;
b) allowing steam sterilant comprising non-condensable gas(es) to interact with the challenge device;
c) measuring over time the temperature of the at least one thermal load and the pressure and/or temperature in the sterilizer;
d) calculating the quantity of non-condensable gas(es) collected in the tube during a selected time interval $\Delta t$ on the basis of the temperature of the at least one thermal load over the selected time interval $\Delta t$, the pressure and/or temperature in the sterilizer over the selected time interval $\Delta t$, the thermal resistance between the tube and the at least one thermal load, the heat capacity of the at least one thermal load and the geometry of the tube;
e) calculating the quantity of steam condensed in the tube during the selected time interval $\Delta t$ on the basis of the heat capacity of the at least one thermal load, the temperature of the at least one thermal load over the selected time interval $\Delta t$, and the specific condensation heat of the steam, wherein the value of specific condensation heat of the steam is either determined on the basis of the measured pressure and/or temperature over time in the sterilizer or used as a constant value independent of temperature dependency; and
f) determining the steam sterilant quality on the basis of the quantity of non-condensable gas(es) collected in the tube during the selected time interval $\Delta t$ and the quantity of steam condensed in the tube during the selected time interval $\Delta t$.

Advantageously this test method allows for measuring the level of non-condensable gases in the steam in a sterilizer. It is to be appreciated that this is significantly different the steam quality test mentioned in the standard EN 285:2006 entitled "Sterilization—Steam Sterilizers—Large Sterilizers" which is merely a general test typically performed upon installation or significant overall of a sterilizer to evaluate compliance of the generated steam with a requirement 13.3.2 of the standard, where samples taken from the steam generation prior to entry into the sterilizer are in simple terms separated into gas and water via a cold water sink and the separated components are collected and measured.

The quantity of non-condensable gas(es) collected in the tube during the selected time interval $\Delta t$ may be calculated in terms of volume ($V_{NCG}$) and/or mass ($m_{NCG}$). The quantity of steam condensed in the tube during the selected time interval $\Delta t$ may be calculated in terms of mass ($m_{steam}$) and/or volume ($V_{steam}$). In regard to the latter typically $V_{steam}$ may be steam, calculated on $m_{steam}$ and density of water. To ensure consistency from determination to determination in a series of measurements with a particular challenge device desirably $V_{NCG}$ and/or $V_{steam}$ are normalized to a selected standard pressure and temperature. Useful standard values for such normalization may be 101.325 kPa and 23° C.

Favorably, the quality of steam sterilant is represented as a percentage of the ratio of the quantity of non-condensable gas(es) collected in the tube during the selected time interval $\Delta t$ and the quantity of steam condensed in the tube during said time interval $\Delta t$. More favorably the ratio is selected from the group consisting of $V_{NCG}/m_{steam}$, $V_{NCG}/V_{steam}$, $m_{NCG}/m_{steam}$ and $m_{NCG}/V_{steam}$.

In some embodiments according to methods of determining steam sterilant quality as described herein, the heat transport from the non-condensable gas(es) located in the bore towards the at least one thermal load may be neglected. This would only lead to insignificant differences in the final results, since the heat transport from the non-condensable gas(es) is typically small as compared to the heat transport from the steam sterilant to the thermal load (due to the condensation energy). Also the heat transport from the at least one thermal load into the ambience may be neglected.

In favorably embodiments according to methods of determining steam sterilant quality as described herein, the heat transport from the non-condensable gas(es) located in the bore towards the at least one thermal load and/or the heat transport from the at least one thermal load into the ambience may be estimated and/or calculated and/or measured and taken into account. This further improves the accuracy of the end results of the methods.

In another aspect of the present disclosure there is provided a system for determining steam sterilant quality of a steam sterilizer where the steam sterilant comprises non-condensable gas(es). The system comprises a) a challenge device comprising
- a tube having a bore, the bore of the tube defining a free space which is open at one end for the entry of steam sterilant and closed at the other end;
- at least one thermal load having a predetermined heat capacity located around the tube, wherein the at least one thermal load contacts directly or indirectly the tube over a contact surface area and there is a predetermined thermal resistance between the tube and the at least one thermal load;
- a temperature sensor adapted to measure the temperature of the at least one thermal load; as well as
- a pressure sensor adapted to measure pressure in the steam sterilizer and/or a temperature sensor adapted to measure the temperature in the steam sterilizer; wherein the challenge device is configured and arranged such that, in use, condensate will flow out of the bore;

b) at least one data collection unit, the at least one data collection unit configured and arranged, such that, in use, it allows for measuring over time the temperature of the at least one thermal load and, as applicable, the pressure and/or temperature in the sterilizer as well as storing measured data together with their corresponding time stamp.

c) at least one data evaluation unit; the at least one data evaluation unit configured and arranged such that, in use, it allows for:
  i) calculating the quantity of non-condensable gas(es) collected in the tube during a selected time interval $\Delta t$ on the basis of the temperature of the at least one thermal load over the selected time interval $\Delta t$, the pressure and/or temperature in the sterilizer over the selected time interval $\Delta t$, the thermal resistance between the tube and the at least one thermal load, the heat capacity of the at least one thermal load and the geometry of the tube;
  ii) calculating the quantity of steam condensed in the tube during the selected time interval $\Delta t$ on the basis of the heat capacity of the at least one thermal load, the temperature of the at least one thermal load over the selected time interval $\Delta t$, and the specific condensation heat of the steam, wherein the value of specific condensation heat of the steam is either determined on the basis of the measured pressure and/or temperature over time in the sterilizer or used as a constant value independent of temperature dependency; and
  iii) determining the steam sterilant quality on the basis of the quantity of non-condensable gas(es) collected in the tube during the selected time interval $\Delta t$ and the quantity of steam condensed in the tube during the selected time interval $\Delta t$.

Systems described herein may be configured such that the challenge device, the at least one data collection unit and the at least one data evaluation unit are provided within in a single appliance. Or alternatively systems described herein may be configured such that the challenge device and the at least one data collection unit are provided within a first appliance and the at least one data evaluation unit in a second appliance. The latter is often more convenient where the first appliance is placed in the sterilizer and the second appliance remains on the outside. Here data may be transferred from the first application to the second application via "hard" connections (wire) or wireless (over IR).

In what terms the quantities of NCGs and steam is calculated is similar to that above for the methods. The same holds true as to the basis for the determination of the steam sterilant quality.

Thermal resistance between the tube and the at least one thermal load generally refers to the thermal resistance in a radial direction, i.e. from the free space of the bore (i.e. the inner surface) through the tube to the at least one thermal load. While the at least one thermal load may be included, to avoid very complicated calculations that do not provide significant enhancement in results, favorably thermal resistance between the tube and the at least one thermal load refers to the thermal resistance from the inner surface of the tube up to but not including the at least one thermal load (i.e. up to the inner surface of the load(s) facing the tube). Moreover, this thermal resistance generally refers to the entire thermal resistance of the tube including any additional layers on the outer and/or inner surface of said tube. For example, the tube may be provided with a foil or sheet of another, possibly thermally insulating, material covering the outer and/or inner surface of the tube. In such a case, the "thermal resistance between the tube and the at least one thermal load" as used in the present disclosure would include the thermal resistance of both the tube itself and the foil or sheeting. This thermal resistance may be determined experimentally by measuring the heat flow through the tube at a given temperature difference or calculated from the specific thermal resistance of the tube material and the geometry of the tube.

Similarly, the heat capacity of the at least one thermal load may be either measured or calculated from the specific heat capacity of the load material and the mass of the load.

Challenge devices of methods and systems described herein, are advantageously configured and arranged such that, in use, condensate will flow out of the bore. For example when a challenge device is positioned within the sterilizer it may be desirably positioned in such a manner that the tube is oriented vertically in order for the non-condensable gas(es) to be collected at a closed top end of the bore while the condensate flows out of the bore at the open bottom end. However, other geometries and/or arrangements may be possible as long as the non-condensable gas(es) can be collected in a predetermined region of the bore and the condensate can flow out of the bore.

Even though the specific condensation heat of the steam is generally viewed a constant material property value, its actual, current value may be determined by measuring temperature and/or pressure over time, since the value of specific condensation heat, strictly speaking, depends on temperature or pressure. Accordingly for more precise results, pressure dependency may be taken into account. In addition working with pressure measurements is particularly favorable due to fast signal of as well as precision of pressure measurements. The actual values for the specific condensation heat may be saved in a look-up table or may be calculated by and interpolated function. In a simple embodiment, the step of determining the specific condensation heat over time simply refers to using an average value of the specific condensation heat.

Preferably, challenge devices of methods and systems described herein comprise a single thermal load. This reduces the complexity and allows for a reduced overall size of the device as well as the costs for manufacturing. If the precision with which the individual parameters such as temperature, pressure and the like are measured is high enough, calculation and determination steps described yield very precise and accurate results even though a single thermal load (and a single temperature sensor associated therewith) is used.

In alternative embodiments, challenge devices may comprise two or more thermal loads and two or more temperature sensors adapted to measure the temperature of each thermal load. While the device utilized in such embodiments may be slightly larger in overall size and more complex, the accuracy of results from calculations and determinations described herein may be even further enhanced by using two or more thermal loads with respective temperature sensors. Moreover, the algorithm underlying the present disclosure does not become significantly more complex in case of more thermal loads. In case two or more thermal loads are used, as indicated favorably the temperature of each thermal load is measured over time and the calculations towards determining quantities of non-condensable gas(es) and steam collected in the tube during a selected time interval Δt are performed on the basis of the measured temperature for each thermal load. In addition it is favorable to space the two or more thermal loads apart from each other by a predetermined distance, and to take this distance(s) into account during the calculations towards determining quantities of non-condensable gas(es) and steam collected in the tube during a selected time interval Δt as well during the determination of the steam sterilant quality on the basis of the said calculated quantities.

Any temperature sensors known to the skilled person may be utilized. It is preferred that the temperature sensors have an accuracy of ±1 K, preferably of ±0.5 K, more preferably of ±0.3 K, most preferably of ±0.1 K.

Summarizing, the following embodiments have been found particularly advantageous and/or desirable:

Embodiment 1

A method for determining steam sterilant quality of a steam sterilizer, the method comprising:
a) providing within the sterilizer a challenge device comprising
   a tube having a bore, the bore of the tube defining a free space which is open at one end for the entry of steam sterilant and closed at the other end;
   at least one thermal load having a predetermined heat capacity located around the tube, wherein the at least one thermal load contacts directly or indirectly the tube over a contact surface area and there is a predetermined thermal resistance between the tube and the at least one thermal load;
   a temperature sensor adapted to measure the temperature of the at least one thermal load; as well as
   a pressure sensor adapted to measure pressure in the steam sterilizer and/or a temperature sensor adapted to measure the temperature in the steam sterilizer;
   wherein the challenge device is configured and arranged such that, in use, condensate will flow out of the bore;
b) allowing steam sterilant comprising non-condensable gas(es) to interact with the challenge device;
c) measuring over time the temperature of the at least one thermal load and the pressure and/or temperature in the sterilizer;

d) calculating the quantity of non-condensable gas(es) collected in the tube during a selected time interval Δt on the basis of the temperature of the at least one thermal load over the selected time interval Δt, the pressure and/or temperature in the sterilizer over the selected time interval Δt, the thermal resistance between the tube and the at least one thermal load, the heat capacity of the at least one thermal load and the geometry of the tube;
e) calculating the quantity of steam condensed in the tube during the selected time interval Δt on the basis of the heat capacity of the at least one thermal load, the temperature of the at least one thermal load over the selected time interval Δt, and the specific condensation heat of the steam, wherein the value of specific condensation heat of the steam is either determined on the basis of the measured pressure and/or temperature over time in the sterilizer or used as a constant value independent of temperature dependency; and
f) determining the steam sterilant quality on the basis of the quantity of non-condensable gas(es) collected in the tube during the selected time interval Δt and the quantity of steam condensed in the tube during the selected time interval Δt.

Embodiment 2

The method of embodiment 1, wherein the quantity of non-condensable gas(es) collected in the tube during the selected time interval Δt is calculated in terms of volume ($V_{NCG}$).

Embodiment 3

The method of embodiment 2, wherein $V_{NCG}$ is normalized to a selected standard pressure and temperature.

Embodiment 4

The method of any one of the previous embodiments, wherein the quantity of non-condensable gas(es) collected in the tube during the selected time interval Δt is calculated in terms of mass ($m_{NCG}$).

Embodiment 5

The method of any one of the previous embodiments, wherein the quantity of steam condensed in the tube during the selected time interval Δt is calculated in terms of mass ($m_{steam}$) and/or volume ($V_{steam}$).

Embodiment 6

The method of embodiment 5, wherein the quantity of steam condensed in the tube during the selected time interval Δt is calculated in terms of volume ($V_{steam}$), wherein the volume of the steam condensed in the tube during said time interval Δt is calculated on the basis of the mass of condensed steam collected in the tube during the selected time interval Δt ($m_{steam}$) and density of water.

Embodiment 7

The method of embodiment 5 or 6, wherein $V_{steam}$ is normalized to a selected standard pressure and temperature.

Embodiment 8

The method of any one of the previous embodiments, wherein the quality of steam sterilant is represented as a percentage of the ratio of the quantity of non-condensable gas(es) collected in the tube during the selected time interval Δt and the quantity of steam condensed in the tube during said time interval Δt.

Embodiment 9

The method of embodiment 8, wherein the ratio is selected from the group consisting of $V_{NCG}/m_{steam}$, $V_{NCG}/V_{steam}$, $m_{NCG}/m_{steam}$ and $m_{NCG}/V_{steam}$ Embodiment 10

The method of any one of the previous embodiments, wherein the heat transport from the non-condensable gas(es) located in the bore towards the at least one thermal load is neglected.

Embodiment 11

The method of any one of the previous embodiments, wherein the heat transport from the at least one thermal load into the ambience is neglected.

Embodiment 12

The method of any one of embodiments 1 to 10, wherein the heat transport from the non-condensable gas(es) located in the bore towards the at least one thermal load and/or the heat transport from the at least one thermal load into the ambience is estimated and/or calculated and/or measured and taken into account.

Embodiment 13

The method of any of the previous embodiments, wherein the challenge device comprises a single thermal load.

Embodiment 14

The method of any one of embodiments 1 to 12, wherein the challenge device comprises two or more thermal loads and two or more temperature sensors adapted to measure the temperature of each thermal load, in particular two or three thermal loads and two or three temperature sensors, respectively, each temperature sensor adapted to measure the temperature of a thermal load.

Embodiment 15

The method of embodiment 14, wherein in step c), the temperature of each thermal load is measured and wherein calculations of steps d) and e) are performed on the basis of the measured temperature for each thermal load.

Embodiment 16

The method of embodiment 14 or embodiment 15, wherein the two or more thermal loads are spaced apart from each other by a predetermined distance and wherein this distance is taken into account during steps d) and/or e) and/or f).

Embodiment 17

The method of any of the previous embodiments, wherein the one or more temperature sensors have an accuracy of ±1 K, in particular ±0.5 K, more particularly ±0.3 K, most particularly ±0.1 K;

and/or
wherein the one or more temperature sensors have a resolution equal to or less than 0.1 K, in particular equal to or less than 0.02 K, more particularly equal to or less than 0.01 K.

Embodiment 18

A system for determining steam sterilant quality of a steam sterilizer where the steam sterilant comprises non-condensable gas(es), the system comprising:
a) a challenge device comprising
   a tube having a bore, the bore of the tube defining a free space which is open at one end for the entry of steam sterilant and closed at the other end;
   at least one thermal load having a predetermined heat capacity located around the tube, wherein the at least one thermal load contacts directly or indirectly the tube over a contact surface area and there is a predetermined thermal resistance between the tube and the at least one thermal load;
   a temperature sensor adapted to measure the temperature of the at least one thermal load; as well as
   a pressure sensor adapted to measure pressure in the steam sterilizer and/or a temperature sensor adapted to measure the temperature in the steam sterilizer;
   wherein the challenge device is configured and arranged such that, in use, condensate will flow out of the bore;
b) at least one data collection unit, the as least one data collection unit configured and arranged, such that, in use, it allows for measuring over time the temperature of the at least one thermal load and, as applicable, the pressure and/or temperature in the sterilizer as well as storing measured data together with their corresponding time stamp.
c) at least one data evaluation unit; the at least one data evaluation unit configured and arranged such that, in use, it allows for:
   i) calculating the quantity of non-condensable gas(es) collected in the tube during a selected time interval Δt on the basis of the temperature of the at least one thermal load over the selected time interval Δt, the pressure and/or temperature in the sterilizer over the selected time interval Δt, the thermal resistance between the tube and the at least one thermal load, the heat capacity of the at least one thermal load and the geometry of the tube;
   ii) calculating the quantity of steam condensed in the tube during the selected time interval Δt on the basis of the heat capacity of the at least one thermal load, the temperature of the at least one thermal load over the selected time interval Δt, and the specific condensation heat of the steam, wherein the value of specific condensation heat of the steam is either determined on the basis of the measured pressure and/or temperature over time in the sterilizer or used as a constant value independent of temperature dependency; and
   iii) determining the steam sterilant quality on the basis of the quantity of non-condensable gas(es) collected in the tube during the selected time interval Δt and the quantity of steam condensed in the tube during the selected time interval Δt.

Embodiment 19

The system of embodiment 18, wherein the challenge device, the at least one data collection unit and the at least one data evaluation unit are provided within in a single appliance.

Embodiment 20

The system of embodiment 18, wherein the challenge device and the at least one data collection unit are provided within a first appliance and the at least one data evaluation unit in a second appliance.

Embodiment 21

The system of any one of embodiments 18 to 20, wherein the quantity of non-condensable gas(es) collected in the tube during the selected time interval $\Delta t$ is calculated in terms of volume ($V_{NCG}$).

Embodiment 22

The system of embodiment 21, wherein $V_{NCG}$ is normalized to a selected standard pressure and temperature.

Embodiment 23

The system of any one of embodiments 18 to 22, wherein the quantity of non-condensable gas(es) collected in the tube during the selected time interval $\Delta t$ is calculated in terms of mass ($m_{NCG}$).

Embodiment 24

The system of any one of embodiments 18 to 23, wherein the quantity of steam condensed in the tube during the selected time interval $\Delta t$ is calculated in terms of mass ($m_{steam}$).

Embodiment 25

The system of embodiment 24, wherein the quantity of steam condensed in the tube during the selected time interval $\Delta t$ is calculated in terms of volume ($V_{steam}$), wherein the volume of the steam condensed in the tube during said time interval $\Delta t$ is calculated on the basis of the mass of steam collected in the tube during the selected time interval $\Delta t$ ($m_{steam}$) and density of water.

Embodiment 26

The system of embodiment 25, wherein $V_{steam}$ is normalized to a selected standard pressure and temperature.

Embodiment 27

The system of any one of embodiments 18 to 26, wherein the quality of steam sterilant is represented as a percentage of the ratio of the quantity of non-condensable gas(es) collected in the tube during the selected time interval $\Delta t$ and the quantity of steam condensed in the tube during said time interval $\Delta t$.

Embodiment 28

The system of embodiment 27, wherein the ratio is selected from the group consisting of $V_{NCG}/m_{steam}$, $V_{NCG}/V_{steam}$, $m_{NCG}/m_{steam}$ and $m_{NCG}/V_{steam}$.

Embodiment 29

The system of any one of embodiments 18 to 28, wherein the heat transport from the non-condensable gas(es) located in the bore towards the at least one thermal load is neglected.

Embodiment 30

The system of any one of embodiments 18 to 29, wherein the heat transport from the at least one thermal load into the ambience is neglected.

Embodiment 31

The system of any one of embodiments 18 to 28, wherein the heat transport from the non-condensable gas(es) located in the bore towards the at least one thermal load and/or the heat transport from the at least one thermal load into the ambience is estimated and/or calculated and/or measured and taken into account.

Embodiment 32

The system of any one of embodiments 18 to 31, wherein the challenge device comprises a single thermal load.

Embodiment 33

The system of any one of embodiments 18 to 31, wherein the challenge device comprises two or more thermal loads and two or more temperature sensors adapted to measure the temperature of each thermal load, in particular two or three thermal loads and two or three temperature sensors, respectively, each temperature sensor adapted to measure the temperature of a thermal load.

Embodiment 34

The system of embodiment 33, wherein the temperature of each thermal load is measured and wherein calculations of steps i) and ii) are performed on the basis of the measured temperature for each thermal load.

Embodiment 35

The system of embodiment 33 or 34, wherein the two or more thermal loads are spaced apart from each other by a predetermined distance and wherein this distance is taken into account during steps i) and/or ii) and/or iii).

Embodiment 36

The system of any one of embodiments 18 to 35, wherein the one or more temperature sensors have an accuracy of ±1 K, in particular ±0.5 K, more particularly ±0.3 K, most particularly of ±0.1 K; and/or wherein the one or more temperature sensors have a resolution equal to or less than 0.1K, in particular equal to or less than 0.02 K, more particularly equal to or less than 0.01 K.

Embodiment 37

The system of any one of embodiments 18 to 36, wherein the tube has along its length a thermal conductivity of 30

$Wm^{-1}K^{-1}$ or less, in particular 25 $Wm^{-1}K^{-1}$ or less, more particularly 20 $Wm^{-1}K^{-1}$ or less.

Embodiment 38

The system of any one of embodiments 18 to 37, wherein the tube has along its cross-section a thermal conductivity greater than 2 $Wm^{-1}K^{-1}$, in particular greater than 4 $Wm^{-1}K^{-1}$.

Embodiment 39

The system of any one of embodiments 18 to 38, wherein the tube has a length of 15 cm or less, in particular 12 cm or less, more particularly 10 cm or less.

Embodiment 40

The system of any one of embodiments 18 to 39, wherein the tube is a hollow cylinder having a wall thickness of 2 mm or less, in particular 1.5 mm or less, more particularly 1 mm or less, even more particularly 0.5 mm or less.

Embodiment 41

The system of any one of embodiments 18 to 40, wherein the bore of the tube has a bore diameter of between 2 mm and 12 mm, in particular between 3.5 mm and 10.5 mm, more particularly between 5 mm and 8 mm.

Embodiment 42

The system of any one of embodiments 18 to 41, wherein the cross section of the tube has an area of 210 $mm^2$ or less, in particular 170 $mm^2$ or less, more particularly 140 $mm^2$ or less.

Embodiment 43

The system of any one of embodiments 18 to 42, wherein the thermal conductivity along the longitudinal axis of the tube does not exceed 120%, in particular 110%, more particularly 105%, of the thermal conductivity in a radial direction.

Embodiment 44

The system of any one of embodiments 18 to 43, wherein the tube is made of metal.

Embodiment 45

The system of embodiment 44, wherein the metal tube comprises one or more selected from: stainless steel; non-rusting steel; CrNi-containing steel; titanium; and titanium alloys.

Embodiment 46

The system of any one of embodiments 18 to 45, wherein the at least one thermal load has a shape substantially corresponding to a cylinder with a bore.

Embodiment 47

The system of embodiment 46, wherein the size and shape of the bore of the at least one thermal load generally corresponds to the outer size and shape of the tube.

Embodiment 48

The system of embodiment 46 or 47, wherein the bore of the at least one thermal load and/or the surface of the bore of the at least one thermal load is shaped such as to intermittently contact the tube.

Embodiment 49

The system of any of embodiments 46 to 48, wherein the surface of the bore of the at least one thermal load comprises at least one laterally or longitudinally extending groove, in particular at least two laterally and/or longitudinally extending grooves, more particularly said grooves being spaced equidistantly from each other.

Embodiment 50

The system of any of embodiments 18 to 49, wherein a foil or sheet of thermally insulating material is provided between the tube and the at least one load.

Embodiment 51

The system of embodiment 50, wherein the foil or sheet comprises a material comprising one or a combination of: polyester, polypropylene, polyacrylonitrile, Kapton, polyurethane, polyamide, polyimide, polyether imide, PTFE, polyvinylchloride, polycarbonate, epoxy resin, polymethylmethacrylate, polyethylene, and polystyrene.

Embodiment 52

The system of embodiment 50 or 51, wherein the foil or sheet comprises a material having a thermal conductivity which is lower than that of the tube, in particular a material having a thermal conductivity of 5 $Wm^{-1}K^{-1}$ or less, more particularly 1 $Wm^{-1}K^{-1}$ or less.

Embodiment 53

The system of any of embodiment 50 to 52, wherein the foil or sheet comprises one or more holes and/or cut-outs to adjust the thermal coupling between the tube and the at least one load.

Embodiment 54

The system of any of embodiments 18 to 53, wherein the at least one load has a heat capacity at 25° C. of at least 0.5 $Jg^{-1}K^{-1}$, in particular at least 0.7 $Jg^{-1}K^{-1}$, more particularly at least 0.85 $Jg^{-1}K^{-1}$.

Embodiment 55

The system of any of embodiments 18 to 54, wherein the at least one load comprises or consists of aluminium.

DETAILED DESCRIPTION

Figure 1:
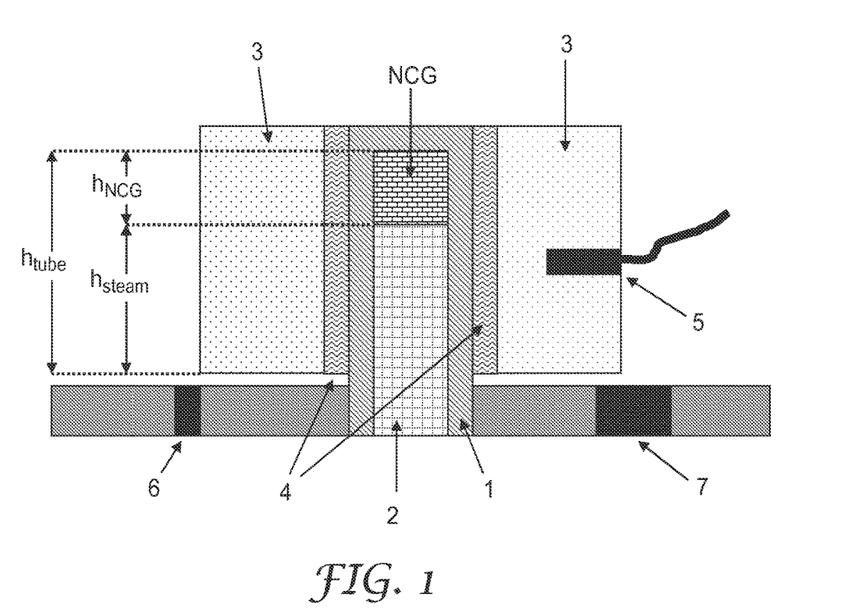
FIG. 1 shows a schematic sketch of a challenge device that may be utilized with methods and systems described herein.

FIG. 1 shows a schematic sketch of a challenge device in cross-section. The challenge device comprises a tube (1) having a bore (2). The bore (2) of the tube (1) defines a free space which is open at the bottom end for the entry of steam sterilant comprising non-condensable gas(es) and closed at the top end and one open end. Since the opening into the bore is located at the bottom of the device, in use, condensate will flow out of the bore. The device further comprises a single thermal load (3) located around the tube (1), wherein a foil (4) is located between the tube and load. There is direct contact between the tube, foil and thermal load, so that the thermal load (3) indirectly contacts the tube over a contact surface area. There is a predetermined (i.e. known or set) thermal resistance from the inner surface of the tube to the inner surface of load (3). The foil is used for specific adjustment of thermal resistance between the tube and the load.

Preferably, the tube material has a thermal conductivity along its length of 30 $Wm^{-1}K^{-1}$ (Watt per meter Kelvin) or less, more preferably of 25 $Wm^{-1}K^{-1}$ or less, and most preferably of 20 $Wm^{-1}K^{-1}$ or less. Thus, such thermal conductivities facilitate minimization or elimination of artefacts due to heat transfer along the length of the tube. It is preferred that tubes have along their cross-section a thermal conductivity greater than 2 $Wm^{-1}K^{-1}$, more preferably greater than 4 $Wm^{-1}K^{-1}$. Here, such thermal conductivities favourably facilitate transport the heat generated during condensation to the thermal loads in a radial direction. For tubes made of an isotropic material or an essentially isotropic material (such as a metal) favourably such the tube materials have a thermal conductivity of 30 $Wm^{-1}K^{-1}$ or less (more favourably of 25 $Wm^{-1}K^{-1}$ or less, and most favourably of 20 $Wm^{-1}K^{-1}$ or less) and a thermal conductivity greater than 2 $Wm^{-1}K^{-1}$ (more favourably greater than 4 $Wm^{-1}K^{-1}$).

Preferably, the material properties, in particular the thermal conductivity, of tubes are essentially isotropic. It is preferred that the thermal conductivity along the longitudinal axis of the tube does not exceed 120%, preferably 110%, and more preferably 105% of the thermal conductivity in a radial direction.

Desirably tubes may be made of metal. Preferably, metal tubes comprise one or a combination of: stainless steel; non-rusting steel; CrNi-containing steel; titanium; and titanium alloys.

Tubes may favourably have a length of 15 cm or less, more preferably 12 cm or less, even more preferably 10 cm or less. Favourably, tubes are hollow cylinders having a wall thickness of 2 mm or less, preferably of 1.5 mm or less, more preferably of 1 mm or less and most preferably of 0.5 mm or less. Favourably, tubes have a bore diameter of between 2 mm and 12 mm, preferably between 3.5 mm and 10.5 mm, more preferably between 5 mm and 8 mm (inclusive the end points). Tubes inclusive wall thickness and bore may favourably have a cross sectional area of 210 $mm^2$ or less, more preferably of 170 $mm^2$ or less, even more preferably of 140 $mm^2$ or less.

Thermal loads preferably have a large heat capacity of preferably equal to or greater than 0.5 $Jg^{-1}K^{-1}$ at 25° C., more preferably of equal to or greater than 0.7 $Jg^{-1}K^{-1}$, even more preferably of equal to or greater than 0.85 $Jg^{-1}K^{-1}$. An exemplary suitable material for the thermal loads is aluminium.

Load(s) preferably have a shape substantially corresponding to a cylinder with a bore. Desirably the size and shape of the bore of the load(s) generally corresponds to the outer size and shape of the tube. This facilitates the provision of a well-defined heat transfer between the tube and the one or more loads. Preferably, the bore of the one or a plurality of loads and/or the surface of the bore of the one or a plurality of loads may be shaped such as to only intermittently contact the tube. This desirably allows an increased control and optimization of the amount of heat transfer between the tube and the load(s). For example, the surface of the bore of the one or more loads may comprise at least one laterally or longitudinally extending groove, preferably at least two or more laterally and/or longitudinally extending grooves, which are preferably spaced equidistantly from each other. In essence, heat transfer then only takes place at the intermittent contact between the load(s) and the tube where no groove is present.

Alternatively or in addition, a foil or sheet of thermally insulating material may be provided between the tube and the one or more loads. Such a foil or sheet may preferably comprise a material comprises one or a combination of: polyester, polypropylene, polyacrylonitrile, Kapton, polyurethane, polyamide, polyimide, polyether imide, PTFE, polyvinylchloride, polycarbonate, epoxy resin, polymethylmethacrylate, polyethylene, and polystyrene. The use of such foils or sheets further aids in providing a well-defined heat transfer between the tube and the one or more loads and/or in controlling or optimizing the amount of heat transfer between the tube and the one or more loads. Foils or sheets preferably comprises a material having a thermal conductivity which is lower than that of the tube. Such materials may have a thermal conductivity of 5 $Wm^{-1}K^{-1}$ or less, more preferably of 1 $Wm^{-1}K^{-1}$ or less. To adjust thermal coupling between the tube and the one or more loads, foils or sheets may favourably comprise several holes and/or cut-outs.

Returning to FIG. 1, when steam comprising non-condensable gas(es) enters the open bottom end of the bore, part of the steam condenses at the comparably cold inner surface of the tube (1) which allows for the condensate being generated to flow out of the bore. Due to the condensation a certain amount of non-condensable gas(es) is collected at the closed top end of the bore (2) (indicated with "NCG" in the sketch). Generally, the amount of heat transferred from the bore (2) of the tube (1) to the load (3) is smaller over that portion of the contact surface area between tube and load over which the bore of the tube is in contact with non-condensable gas(es), than steam, since the condensation of the steam provides for an increased energy input into the thermal load due to condensation heat. Thus, the course of the temperature of the thermal load over time provides information about the amount of non-condensable gas(es) versus the amount of condensed steam. This allows for a determination of steam sterilant quality on the basis of the quantity of non-condensable gas(es) and the quantity of condensed steam. The temperature of the thermal load is measured by means of a temperature sensor (5).

The exemplary embodiment shown in FIG. 1 is also provided with a temperature sensor (6) as well as a pressure sensor (7) which allow for the measurement of temperature and pressure, respectively, inside the sterilizer (i.e. measurement of "unchallenged" temperature and pressure). Favorably challenge devices include both sensors, however it is possible to use just a temperature sensor or alternative just a pressure sensor. If a single sensor is being used desirably it is a pressure sensor, because pressure sensors are typically more precise and have faster response times. The temperature inside the sterilizer can be derived from measured pressure data, and in fact due to the mentioned favorable features of pressure sensor, this derived temperature will allow for more accuracy results. The skilled person knows how to derive temperature from measure pressure data.

Pressure sensors suitable for use include those available on the market which withstand high pressures that may be present within a sterilizer during a typical sterilization cycle or even slightly higher (e.g. up to 4 bar absolute). Also it is desirable to employ pressure sensors which have a low long term drift and that are calibrated and temperature compensated to ensure high accuracy.

Temperature sensors used to measure the temperatures at the load(s) and/or in the sterilizer favorably have an accuracy of ±1 K, more favorably of ±0.5 K, even more favorably of ±0.3 K, most favorably of ±0.1 K. Temperature sensors used to measure the temperatures at the load(s) and/or in the sterilizer favorably have a high resolution, for example equal to or less than 0.1K, more favorably equal to or less than 0.02 K, and most favorably equal to or less than 0.01 K. Also it is desirable to employ temperature sensors which have a low long term drift and that are calibrated to ensure high accuracy.

In the following, examples of calculations used to determine quantities non-condensable gas(es) versus the amount of steam based on the measured temperature of the load(s) and measured pressure and/or temperature in the sterilizer, the results of the calculations are in turn used to provide a measure of steam sterilant quality. Reference is made to the exemplary challenge device embodiment shown in FIG. 1, where the cylindrical tube has the height $h_{Tube}$ starting from the position adjacent to the lower edge of the thermal load up to the inner closed end of the bore. The innermost portion of the tube having a height $h_{NCG}$ is filled with non-condensable gas(es) and the outer part of the tube having a height $h_{steam}$ is filled with steam, not yet condensed. It is to be understood that NCGs collected at the innermost portion of the tube due to the continuous steam flow inwardly which in turn pushes NCGs inwardly. In the following, temperature in the sterilizer is referred to as "steam temperature" and as mentioned above this may be either measured directly using an appropriate temperature sensor or derived from pressure data measured using an appropriate pressure sensor.

The total condensation energy of the steam condensed in the tube $E_{steam}$ can be calculated as follows:

$$E_{Steam}(t)(T_{Load}(t)-T_0) \cdot C_{Load} \qquad (I)$$

with $C_{Load}$=heat capacity of thermal load
and $T_{Load}$=temperature of thermal load
and $T_0$=temperature of thermal load at the beginning of the sterilization process The heating power of the steam $P_{Steam}$ in the tube can be calculated from the derivation of the energy $E_{Steam}$ with respect to time:

$$P_{Steam}(t) = \frac{dE_{Steam}(t)}{dt} = \frac{dT_{Load}(t)}{dt} \cdot C_{Load} \qquad (II)$$

The heating power $P_{Steam}$ can also be calculated from the steam temperature $T_{STEAM}$ and the actual load temperature $T_{Load}$ assuming that the inner surface area of the tube has the temperature of the steam:

$$P_{Steam}(t) = \frac{T_{Steam}(t) - T_{Load}(t)}{R} \qquad (III)$$

with R=thermal resistance between the tube and the at least one thermal load With the abbreviation $\Delta(t)=T_{Steam}(t)-T_{Load}(t)$ equation (III) can be written as:

$$P_{Steam}(t) = \frac{\Delta T(t)}{R} \qquad (IV)$$

The thermal resistance R can be described as the quotient of the specific thermal resistance r of the tube and the contact area A between the load and the tube $$R = \frac{r}{A} \qquad (V)$$

In case of a cylindrical tube which is in contact with the thermal load of the entire surface thereof as sketched in FIG. 1 the contact area A is a product of the height of the load h and the circumference of the tube U $$A = h \cdot U \qquad (VI)$$

In case non-condensable gas (NCG) is collected in the tube, it will insulate a part of the tube (or at least reduce heat transfer there from). Only that part of the tube that is filled with steam and is in thermal contact with the load will contribute to the heating power $P_{Steam}$. This height is here called $h_{Steam}$. Taking this into account with equation (IV, V, VI) one obtains:

$$P_{Steam}(t) = \frac{\Delta T(t)}{r} \cdot h_{Steam} \cdot U \qquad (VII)$$

Equation (VII) can be transposed to $h_{Steam}$ resulting in:

$$h_{Steam}(t) = \frac{P_{Steam}(t) \cdot r}{\Delta T(t) \cdot U} \qquad (VIII)$$

Using equation (II) yields:

$$h_{Steam}(t) = \frac{\frac{dT_{Load}(t)}{dt} \cdot C_{Load} \cdot r}{\Delta T(t) \cdot U} \qquad (IX)$$

Equation (IX) generally shows that $h_{Steam}$ can be calculated from temperature measurements of the load and measured or derived temperature of the steam.

The volume of NCG $V_{NCG}$ can be calculated from the inner volume of the tube $V_{Tube}$ ($h_{Tube}$ height of tube, $r_{Tube}$ inner radius of tube):

$$V_{Tube} = h_{Tube} \cdot \pi \cdot r_{Tube}^2 \tag{X}$$

Assuming a clear separation of steam and NCG we get:

$$h_{Tube} = h_{Steam} + h_{NCG} \tag{XI}$$

Transposing to $h_{NCG}$ yields:

$$h_{NCG} = h_{Tube} - h_{Steam} \tag{XII}$$

Using equation (IX) e.g. we get height of NCG in the tube over time:

$$h_{NCG}(t) = h_{Tube} - \frac{\frac{dT_{Load}(t)}{dt} \cdot C_{Load} \cdot r}{\Delta T(t) \cdot U} \tag{XIII}$$

Now the volume of non-condensable gas(es) $V_{NCG}$ can be calculated for example with following equation:

$$V_{NCG}(t) = h_{NCG}(t) \cdot \pi \cdot r_{Tube}^2 \tag{XIV}$$

To make the initially calculated volume of NCG $V_{NCG}$ independent of pressure and temperature, it is desirably to normalize the value.

For example, using the "ideal gas law"

$$p \cdot V = n \cdot R_m \cdot T \tag{XV}$$

the volume of NCG at a normal pressure and temperature, in particular at 101325 Pa and 23° C., $V_{NCG\_normal}$ can be calculated $$V_{NCG\_normal} = V_{NCG\_in\_ETS} \cdot \frac{p_{NCG(=Chamber)}}{p_{normal}} \cdot \frac{T_{normal}}{T_{NCG(=Chamber/Tube)}} \tag{XVI}$$

From the volume one can also derive the mass of NCG $m_{NCG}$, for example using the following formula:

$$m_{NCG} = \frac{V_{NCG\_normal}}{24.3 \text{ l/mol}} \cdot m_{mol} \tag{XVIb}$$

where $m_{mol}$ is 29 g/mol and 24.3 l/mol represents the volume of 1 mol of gas under normal conditions, i.e. at 101.325 kPa and 23° C.

The mass of steam, which is condensed in the tube can be obtained by using the equation:

$$E_{Steam} = \Delta H_{Steam} \cdot m_{Steam} \tag{XVII}$$

with $$\Delta H_{Steam} \approx 39 \ \frac{\text{kJ}}{\text{mol}} = \text{specific condensation heat}$$

$m_{Stream}$ = mass of steam in mol
and equation (I):

$$E_{Steam}(t) = (T_{Load}(t) - T_0) \cdot C_{Load} \stackrel{!}{=} \Delta H_{Steam} \cdot m_{Steam} \tag{XVIII}$$

Transposing results in:

$$m_{Steam}(t) = \frac{(T_{Load}(t) - T_0) \cdot C_{Load}}{\Delta H_{Steam}} \tag{XIX}$$

For higher accuracy instead of using a constant value of $\Delta H_{steam}$ independent of the temperature, a value for $\Delta H_{Steam}$ may be determined on the basis of measured temperature (or, if applicable, determined via measured pressure), yielding $$m_{Steam}(t) = \frac{(T_{Load}(t) - T_0) \cdot C_{Load}}{\Delta H_{Steam}(T_{Steam})} \tag{XIXb}$$

If desired, the quantity of condensed steam can be given in terms of volume ($V_{steam}$) where the $V_{steam}$ is equal to the $m_{steam}$ divided by the density of water.

As can be recognized from above, the quantities of NCG and steam collected in the tube during a selected time interval $\Delta t$ may be calculated in terms of either volume or mass, by using challenge devices as described herein, measured temperature measurements of the thermal load(s) and measured pressure and/or temperature in the sterilizer. Any appropriate ratio of these determined quantities of NCG and steam (e.g. $V_{NCG}/m_{steam}$, $V_{NCG}/V_{steam}$, $m_{NCG}/m_{steam}$ and $m_{NCG}/V_{steam}$) may serve as a good measure for steam quality. However it is desirable to use ratio $V_{NCG}/m_{steam}$ or $V_{NCG}/V_{steam}$ since the determination of mass of NCGs required additional calculations while mass and volume of steam are essentially the same value since the density of water is one. Making reference to section 13.3.2 DIN EN 285, a value of greater than 3.5% V/V would seem to be an indicator of poor quality (as well as an indicator of some potential issue(s) with either the steam generator or sterilizer). Clearly a value approaching 0% would be ideal in terms of efficacy of sterilization. To allow for a desirable indicator of efficacy of sterilization, correlation studies may be made with side-by-side quality of steam determinations as described herein together with microbicidal efficiency determinations so that a particular value steam quality determined during sterilization may be correlated to a particular level of residual microbial activity after sterilization.

The aforesaid example refers to a case where a single load is used, where its temperature as well as the "temperature of steam" are used in the equations. Again temperature in sterilizer may be directly measured or derived from measured pressure in the sterilizer. Although not shown in the equations, as mentioned above the skilled person knows how to derive temperature from pressure data, and the skilled person will know how to use measured pressure data and appropriately incorporate such data into the calculations illustrated by the equations shown above. The aforesaid calculations were made using data of and from a challenge device having a tube with a bore having a constant diameter along its length. However, it will be recognized by the skilled person that the equations and calculations shown above may be appropriately adjusted in case of other geometries, e.g. a conical-like tube bore.

Methods in accordance may be applied to cases where challenge devices having two or more than one thermal loads are used.

Figure 2:
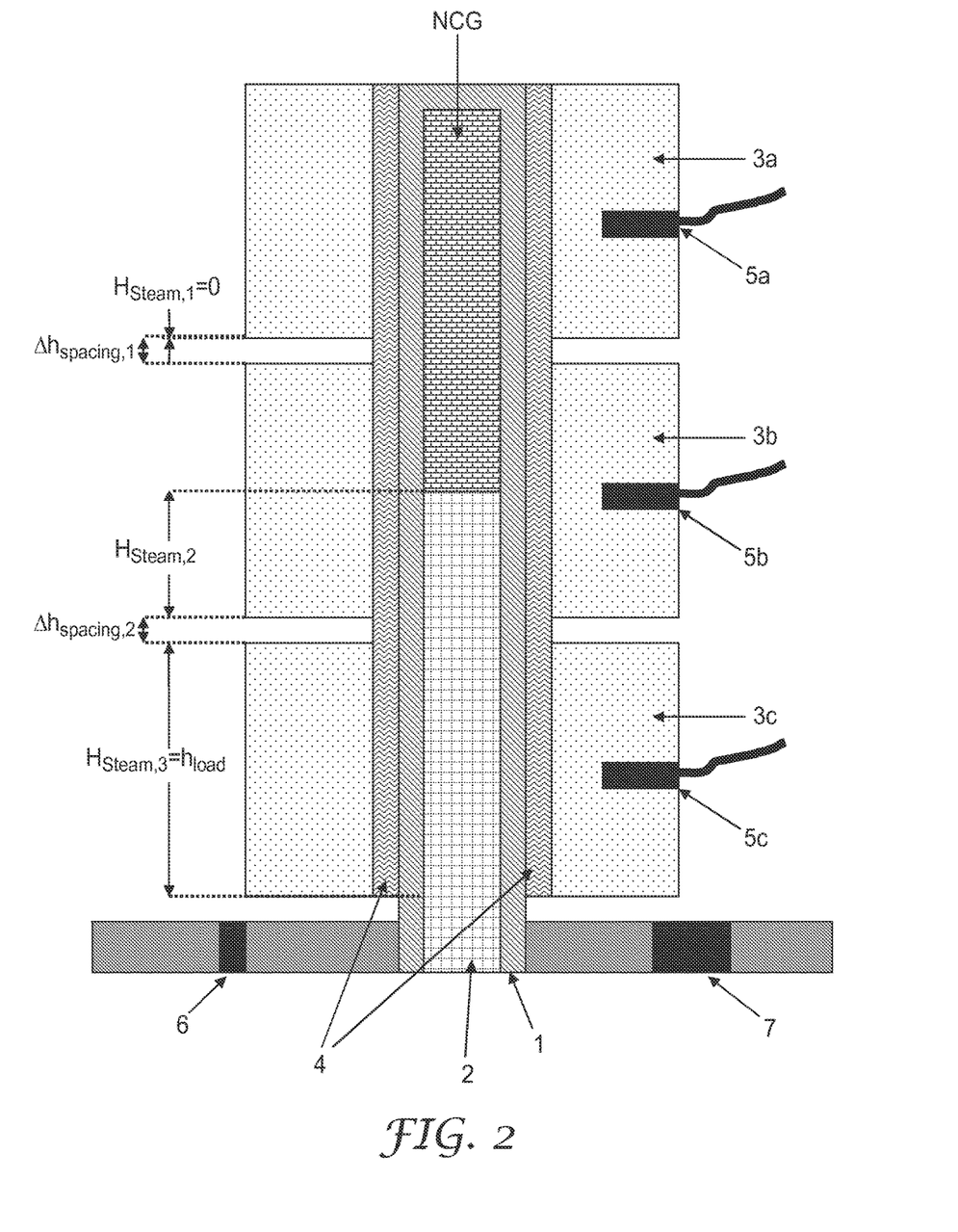
FIG. 2 shows a schematic sketch of another challenge device that may be utilized with methods and systems described herein.

FIG. 2 shows a sketch of an exemplary challenge device including more than one thermal load. As in the first exemplary embodiment the device include a tube (1) but now three loads (3a), (3b) and (3c) located around the tube. Again there is a foil (4) between the tube and the loads. Favorably, the temperature of each thermal load is measured by means of a temperature sensor (5a, 5b, 5c) associated with an individual load. Similar to the exemplary challenge device shown in FIG. 1, the exemplary challenge device of FIG. 2 favorably includes a temperature sensor (6) as well as a pressure sensor (7) which allow for the measurement of temperature and pressure, respectively, inside the sterilizer (i.e. measurement of "unchallenged" temperature and pressure).

In such a case the amount of non-condensable gas(es) can be calculated in the same way as shown above. It just has to be done for every load, i.e. the determination of the height of the step according to equation (IX) is solved for each and every load. In case, the load is adjacent to a portion of the tube where there is only NCG (as is the case for load (3a) in FIG. 2), $h_{Steam}$ will be equal to zero. In case the load is adjacent to a portion of the tube where there is only steam (as is the case for load (3c) in FIG. 2), $h_{Steam}$ will be equal to the height of the load. In case the load is adjacent to a portion of the tube where there is both NCG and steam (as is the case for load (3b) in FIG. 2) the value of $h_{Steam}$ will be between zero and the height of the load in proportion to the amounts of NCG and steam (in FIG. 2 the amount of NCG and steam is 1 to 1 and thus the $h_{Steam}$ is one half the height of the load).

Now $h_{Steam}$ for every load which is covered at least in part with steam has to be summed up, resulting in $h_{Steam, total}$ for the whole tube (s. equation (XX)), considering the spacing between the loads (which would preferably be between about 1 mm and about 4 mm).

$$h_{Steam,total}(t) = \sum_i (h_{Steam,i}(t) + \Delta h_{Spacing,i}) \quad (XX)$$

This value can then be used for the further calculations in analogy to the calculations shown above.

The calculation of the total amount of condensed steam is similar to equation (XIX). The amount of condensed steam of every load may be summed up as shown in the following equation:

$$m_{Steam}(t) = \sum_i \frac{(T_{Load,i}(t) - T_{0,i}) \cdot C_{Load,i}}{\Delta H_{Steam}} \quad (XIXB)$$

Evidently, other modifications to the above algorithm may be made without departing from the scope of the present disclosure.

Figure 3:
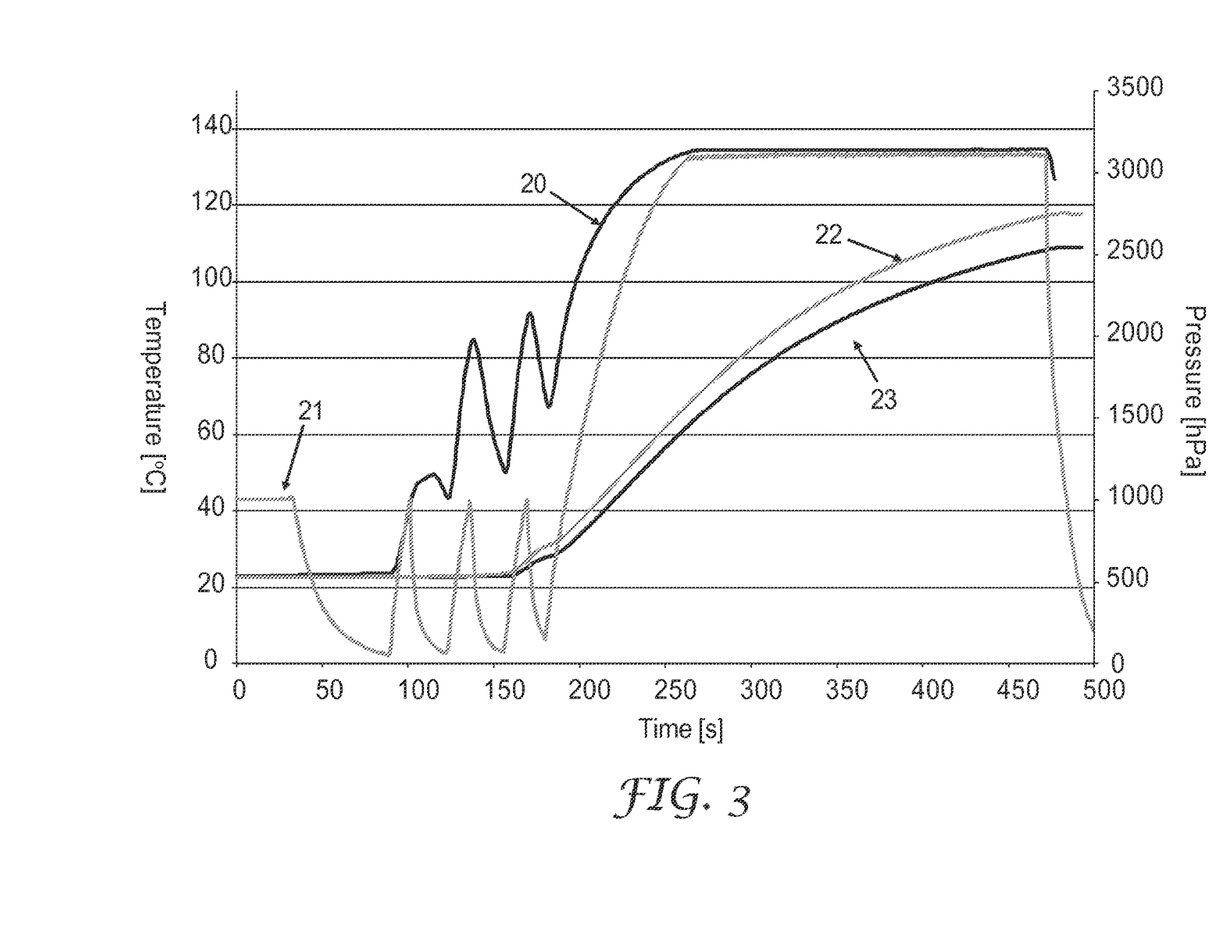
FIG. 3 shows a curve of measured parameter for a typical sterilization run using an exemplary challenge device of the type described herein.

FIG. 3 shows curves of measured parameter for a typical sterilization run using an exemplary challenge device having two thermal loads with a temperature sensor at each load as well temperature and pressure sensor for measuring the temperature and pressure in the sterilizer. The graph shows the measured temperature inside the sterilizer (but outside of the tube bore) over time (curve 20); the measured pressure (curve 21) inside the sterilizer over time as well as the measured temperature at lower, outer thermal load (curve 22) and the inner, upper thermal load (curve 23) over time. The sterilization run includes three purges, i.e. evacuation and (partially) filling with steam, and after the last evacuation, the sterilization phase is started where the sterilizer is pumped with steam sterilant so that the temperature within the sterilizer reaches 134° C.

Figure 4:
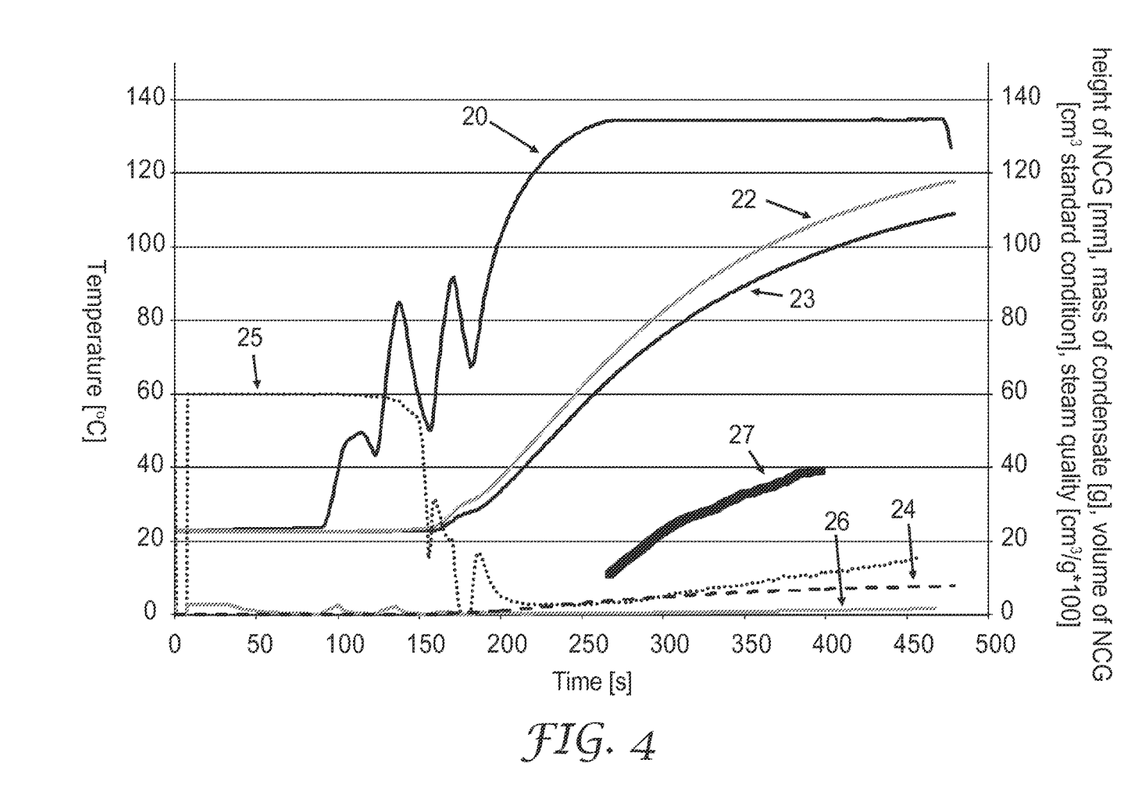
FIG. 4 shows the curve of FIG. 3 including various determined data using exemplary calculations of the type described herein.

FIG. 4 shows the same measured temperature data shown in FIG. 3 (curves 20, 22, 23) together some calculated parameters. One of these is the mass of condensate, i.e. condensed steam, during the cycle over time (curve 24). Another two of these include the height of NCG-level in the tube over time (curve 25) and volume of NCG over time normalized to 101.325 kPa and 23° C. (curve 26). The latter curve is very low relative to the former due to inter alia the normalization. It will be appreciated that during the purging phase the amount of NCGs in the sterilizer and correspondingly in the bore of the tube falls dramatically, and as shown in FIG. 4 during the sterilization phase the amount of NCGs in the tube slowly climbs as ever increasing amounts of NCGs are collected within the tube over time. Ideally when there were no NCGs in the steam sterilant and the sterilizer is perfectly sealed and all NCGs were removed during purging phase, the amount of NCGs found in the sterilizer during a sterilization phase would be or would approach zero. The curve labeled "curve 27" in FIG. 4 is the calculated steam quality (NCG concentration) derived from the volume of the NCG at ambient/standard conditions and the volume of condensate. It should be appreciated that the illustrated experiment in FIG. 4 represents a "non-ideal" run where the NCG concentration is unfavorably high. High NCG concentrations can be the result of a number of factors including e.g. leakage along the steam-inlet pipe installation and/or adaptors of the sterilization chamber.

Figure 5:
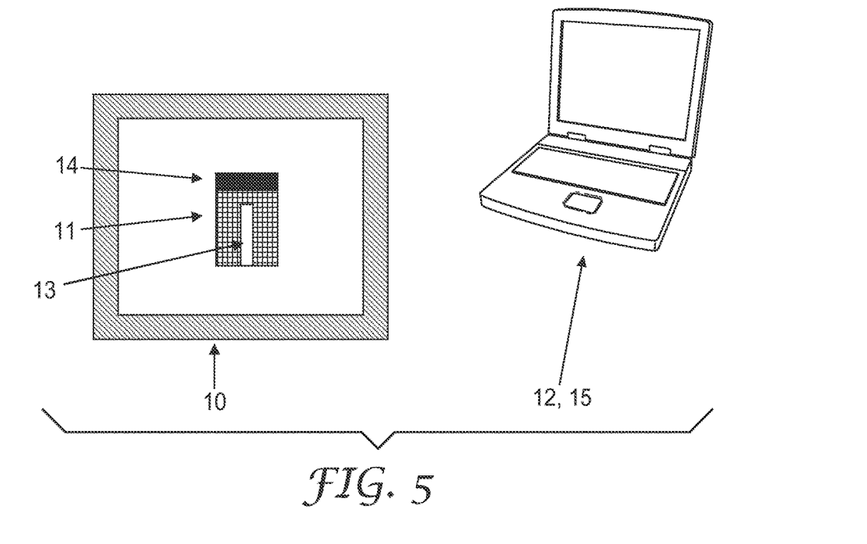
FIG. 5 shows a schematic sketch of a system in accordance with an aspect of the present disclosure.
Figure 6:
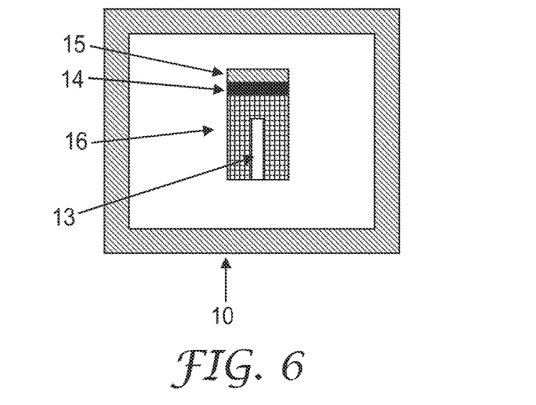
FIG. 6 shows a schematic sketch of another system described herein in accordance with an aspect of the present disclosure.

FIGS. 5 and 6 show schematic sketches of configurations of systems in accordance with the disclosure in relation to a steam sterilizer (10). In one configuration as shown in FIG. 5, a system may be composed of two appliances, one appliance (11) including the challenge device (13) and data collection unit (14) to be inserted into the chamber of a steam sterilizer and the second appliance (12) including a data evaluation unit (15). Data evaluation units generally include a visual display. They may be computers. Alternatively they may be handheld computing devices or any other suitable computing devices. Typically data is transferred automatically from the data collection unit to data evaluation unit either through wires or wireless. Evaluation units may be mounted onto an outer surface of the sterilizer or be detached from the sterilizer (as shown in FIG. 5). In an alternative configuration, such as that shown in FIG. 6, a system may be a single appliance (16) including the challenge device (13), data collection unit (14) as well as the data evaluation unit (15). Such an appliance favorably includes a visual display.

Methods and systems described herein provides several advantages over the prior art. For example, methods and systems described herein can effectively make use of challenge devices requiring only a single or a low number of loads (e.g. two or three). This allows for a simplification of the challenge device, which accordingly at the same time, provides for the use of less sensors. In fact, in the most simple embodiments where the challenge device has one load, the device may only comprise two temperature sensors or a single temperature and a single pressure sensor. This is advantageous in that a low number of interfering heat bridges are generated and the resulting data analysis is much easier. Thus, methods and systems described herein allow for the use of challenge devices that are less expensive, easier to build, require less electronics and may be significant smaller in size. Finally, a quantitative assessment of the steam quality may be achieved using a comparably simple device.

The invention claimed is:
1. Method for determining steam sterilant quality of a steam sterilizer, the method comprising:
   a) providing within the sterilizer a challenge device comprising
      a tube having a bore, the bore of the tube defining a free space which is open at one end for the entry of steam sterilant and closed at the other end;

at least one thermal load having a predetermined heat capacity located around the tube, wherein the at least one thermal load contacts directly or indirectly the tube over a contact surface area and there is a predetermined thermal resistance between the tube and the at least one thermal load;

a temperature sensor adapted to measure the temperature of the at least one thermal load; as well as a pressure sensor adapted to measure pressure in the steam sterilizer and/or a temperature sensor adapted to measure the temperature in the steam sterilizer;

wherein the challenge device is configured and arranged such that, in use, condensate will flow out of the bore;

b) allowing steam sterilant comprising non-condensable gas(es) to interact with the challenge device;

c) measuring over time the temperature of the at least one thermal load and the pressure and/or temperature in the sterilizer;

d) calculating the quantity of non-condensable gas(es) collected in the tube during a selected time interval $\Delta t$ on the basis of the temperature of the at least one thermal load over the selected time interval $\Delta t$, the pressure and/or temperature in the sterilizer over the selected time interval $\Delta t$, the thermal resistance between the tube and the at least one thermal load, the heat capacity of the at least one thermal load and the geometry of the tube;

e) calculating the quantity of steam condensed in the tube during the selected time interval $\Delta t$ on the basis of the heat capacity of the at least one thermal load, the temperature of the at least one thermal load over the selected time interval $\Delta t$, and the specific condensation heat of the steam, wherein the value of specific condensation heat of the steam is either determined on the basis of the measured pressure and/or temperature over time in the sterilizer or used as a constant value independent of temperature dependency; and f) determining the steam sterilant quality on the basis of the quantity of non-condensable gas(es) collected in the tube during the selected time interval $\Delta t$ and the quantity of steam condensed in the tube during the selected time interval $\Delta t$.

2. The method of claim 1, wherein the quantity of non-condensable gas(es) collected in the tube during the selected time interval $\Delta t$ is calculated in terms of volume ($V_{NCG}$) and/or mass ($m_{NCG}$).

3. The method of claim 1, wherein the quantity of steam condensed in the tube during the selected time interval $\Delta t$ is calculated in terms of mass ($m_{steam}$) and/or volume ($V_{steam}$).

4. The method of claim 1, wherein the quality of steam sterilant is represented as a percentage of the ratio of the quantity of non-condensable gas(es) collected in the tube during the selected time interval $\Delta t$ and the quantity of steam condensed in the tube during said time interval $\Delta t$, in particular the ratio is selected from the group consisting of $V_{NCG}/m_{steam}$, $V_{NCG}/V_{steam}$, $m_{NCG}/m_{steam}$ and $m_{NCG}/V_{steam}$.

5. The method of claim 1, wherein the challenge device comprises a single thermal load, or wherein the challenge device comprises two or more thermal loads and two or more temperature sensors adapted to measure the temperature of each thermal load, in particular two or three thermal loads and two or three temperature sensors, respectively, each temperature sensor adapted to measure the temperature of a thermal load.

6. A system for determining steam sterilant quality of a steam sterilizer where the steam sterilant comprises non-condensable gas(es), the system comprising:
   a) a challenge device comprising
      a tube having a bore, the bore of the tube defining a free space which is open at one end for the entry of steam sterilant and closed at the other end;
      at least one thermal load having a predetermined heat capacity located around the tube, wherein the at least one thermal load contacts directly or indirectly the tube over a contact surface area and there is a predetermined thermal resistance between the tube and the at least one thermal load;
      a temperature sensor adapted to measure the temperature of the at least one thermal load; as well as
      a pressure sensor adapted to measure pressure in the steam sterilizer and/or a temperature sensor adapted to measure the temperature in the steam sterilizer;
      wherein the challenge device is configured and arranged such that, in use, condensate will flow out of the bore;
   b) at least one data collection unit, the as least one data collection unit configured and arranged, such that, in use, it allows for measuring over time the temperature of the at least one thermal load and, as applicable, the pressure and/or temperature in the sterilizer as well as storing measured data together with their corresponding time stamp;
   c) at least one data evaluation unit; the at least one data evaluation unit configured and arranged such that, in use, it allows for:
      i) calculating the quantity of non-condensable gas(es) collected in the tube during a selected time interval $\Delta t$ on the basis of the temperature of the at least one thermal load over the selected time interval $\Delta t$, the pressure and/or temperature in the sterilizer over the selected time interval $\Delta t$, the thermal resistance between the tube and the at least one thermal load, the heat capacity of the at least one thermal load and the geometry of the tube;
      ii) calculating the quantity of steam condensed in the tube during the selected time interval $\Delta t$ on the basis of the heat capacity of the at least one thermal load, the temperature of the at least one thermal load over the selected time interval $\Delta t$, and the specific condensation heat of the steam, wherein the value of specific condensation heat of the steam is either determined on the basis of the measured pressure and/or temperature over time in the sterilizer or used as a constant value independent of temperature dependency; and
      iii) determining the steam sterilant quality on the basis of the quantity of non-condensable gas(es) collected in the tube during the selected time interval $\Delta t$ and the quantity of steam condensed in the tube during the selected time interval $\Delta t$.

7. The system of claim 6, wherein the challenge device comprises a single thermal load, or wherein the challenge device comprises two or more thermal loads and two or more temperature sensors adapted to measure the temperature of each thermal load, in particular two or three thermal loads and two or three temperature sensors, respectively, each temperature sensor adapted to measure the temperature of a thermal load.

8. The system of claim 6, wherein the tube has along its length a thermal conductivity of 30 $Wm^{-1}K^{-1}$ or less; and/or wherein the tube has along its cross-section a thermal conductivity greater than 2 $Wm^{-1}K^{-1}$; and/or wherein the thermal conductivity along the longtidunal axis of the tube does exceed 120% of the thermal conductivity in a radial direction.

9. The system of claim 6, wherein the tube has a length of 15 cm or less; and/or wherein the tube is a hollow cylinder having a wall thickness of 2 mm or less; and/or wherein the bore of the tube has a bore diameter of between 2 mm and 12 mm; and/or wherein the cross section of the tube has an area of 210 $mm^2$ or less.

10. The system of claim 6, wherein the tube is made of metal, in particular the tube is a metal tube comprising one or more selected from: stainless steel; non-rusting steel; CrNi-containing steel; titanium; and titanium alloys.

11. The system of claim 6, wherein the at least one thermal load has a shape substantially corresponding to a cylinder with a bore.

12. The system of claim 11, wherein the size and shape of the bore of the at least one thermal load generally corresponds to the outer size and shape of the tube.

13. The system of claim 11, wherein the bore of the at least one thermal load and/or the surface of the bore of the at least one thermal load is shaped such as to intermittently contact the tube.

14. The system of claim 6, wherein a foil or sheet of thermally insulating material is provided between the tube and the at least one load, in particular said foil or sheet comprises a material having a thermal conductivity which is lower than that of the tube.

15. The system of claim 6, wherein the at least one load has a heat capacity at 25° C. of at least 0.5 $Jg^{-1}K^{-1}$.

* * * * *